(12) United States Patent
Hofmann

(10) Patent No.: US 12,156,758 B2
(45) Date of Patent: Dec. 3, 2024

(54) METHOD FOR ACTUATING A MEDICAL IMAGING DEVICE

(71) Applicant: Siemens Healthcare GmbH, Erlangen (DE)

(72) Inventor: Christian Hofmann, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 562 days.

(21) Appl. No.: 17/473,075

(22) Filed: Sep. 13, 2021

(65) Prior Publication Data

US 2022/0087630 A1 Mar. 24, 2022

(30) Foreign Application Priority Data

Sep. 23, 2020 (DE) ................ 10 2020 211 944.9

(51) Int. Cl.
*A61B 6/00* (2024.01)
*A61B 6/03* (2006.01)

(52) U.S. Cl.
CPC .............. *A61B 6/486* (2013.01); *A61B 6/032* (2013.01); *A61B 6/5264* (2013.01); *A61B 6/541* (2013.01)

(58) Field of Classification Search
CPC ................... A61B 6/032; A61B 6/486; A61B 6/5258–541
See application file for complete search history.

(56) References Cited

U.S. PATENT DOCUMENTS

| 2005/0201509 A1 | 9/2005 | Mostafavi et al. |
| 2017/0238895 A1 | 8/2017 | Hofmann |
| 2019/0005647 A1 | 1/2019 | Hofmann |
| 2020/0121266 A1 | 4/2020 | Hofmann |
| 2020/0121274 A1 | 4/2020 | Hofmann |
| 2020/0163639 A1* | 5/2020 | De Man .................... G06T 7/20 |
| 2020/0265177 A1 | 8/2020 | Raupach |

FOREIGN PATENT DOCUMENTS

| CN | 104939861 B | 11/2018 |
| DE | 102012201835 A1 | 8/2013 |
| DE | 102016202605 A1 | 8/2017 |
| DE | 102018217886 A1 | 4/2020 |
| DE | 102018217888 A1 | 4/2020 |
| DE | 102019202287 A1 | 8/2020 |

* cited by examiner

*Primary Examiner* — Carolyn A Pehlke
(74) *Attorney, Agent, or Firm* — Harness, Dickey & Pierce, P.L.C.

(57) ABSTRACT

A method is for actuating a medical imaging device for generating an image data set of a patient's measurement region affected by respiratory movement. In an embodiment, the method includes provisioning a respiratory curve of the patient describing the respiratory movement of the patient over a respiratory cycle; automatically deriving a measurement parameter based upon the respiratory curve, the measurement parameter derived determining a temporal resolution of the at least one slice image data set; and actuating the medical imaging device to generate the image data set based upon the measurement parameter. For a z position, a plurality of projection data sets from various projection angles are acquired with relative rotational movements between a radiation source of the medical device and the patient. The at least one slice image data set of the image data set is generated based upon the plurality of projection data sets acquired.

20 Claims, 4 Drawing Sheets

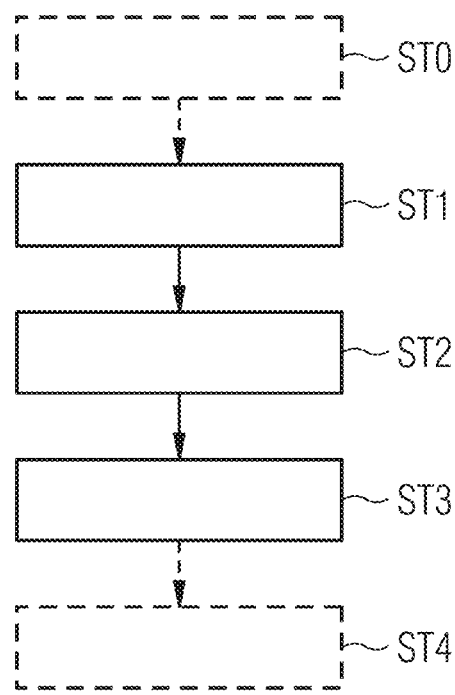

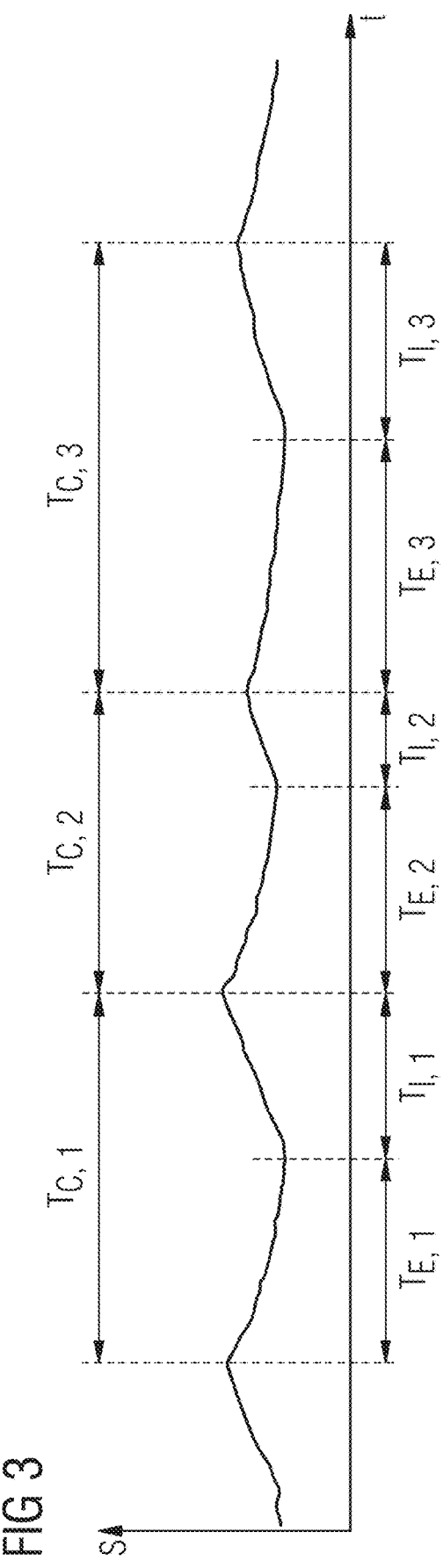
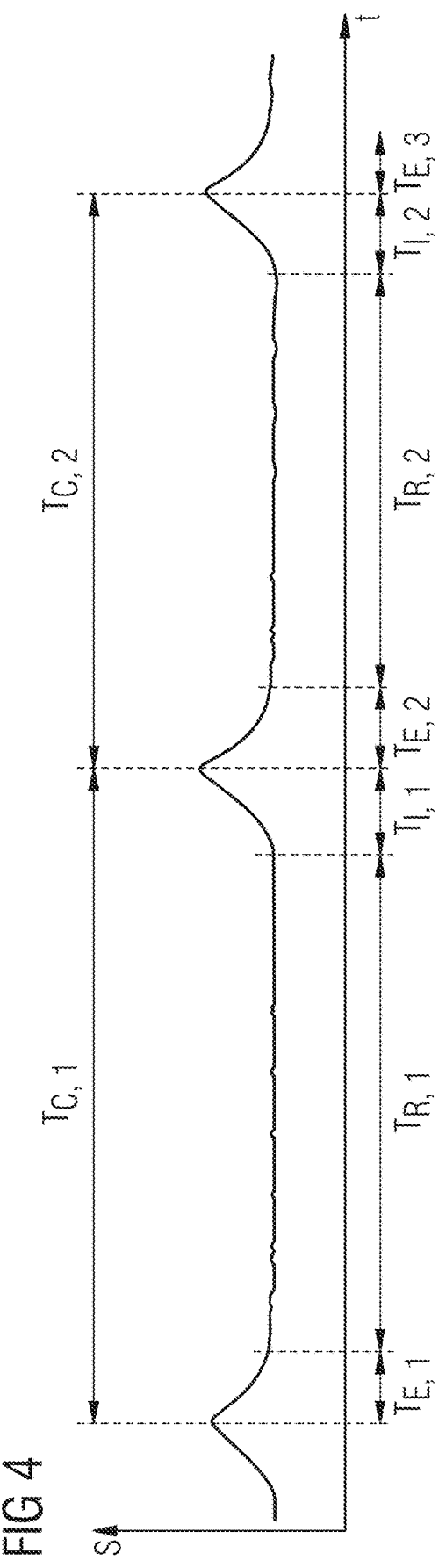

METHOD FOR ACTUATING A MEDICAL IMAGING DEVICE

PRIORITY STATEMENT

The present application hereby claims priority under 35 U.S.C. § 119 to German patent application number DE102020211944.9 filed Sep. 23, 2020, the entire contents of which are hereby incorporated herein by reference.

FIELD

Example embodiments of the invention generally relate to a method for actuating a medical imaging device for generating an image data set of a patient's measurement region, to an associated apparatus for actuating a medical imaging device, to the associated medical imaging device and to an associated computer program product. Example embodiments of the invention furthermore generally relate to a training method for providing a trained function for application in a method for actuating a medical imaging device, to an associated training apparatus, and to an associated computer program product.

BACKGROUND

Three-dimensional (3D) image data sets of a measurement region with an extent in the z direction are used for planning the irradiation of a patient for example with pulmonary or abdominal carcinoma. Via a medical imaging device, in particular a computed tomograph, it is in particular possible during an imaging examination to acquire projection data sets from which the 3D image data sets can be reconstructed. The imaging examination via a computed tomograph conventionally requires ionizing X-rays. Methods for sampling an object under examination with a medical imaging device, in particular for example via a computed tomography system (CT system), are generally known. Circular scans, sequential circular scans with sequential advance or helical scans with continuous table advance are, for example, used for this purpose. Other types of scan which are not based on circular movements are also possible. With the assistance of at least one radiation source and at least one opposing detector, absorption data from the patient is captured from different capture angles, hereinafter also denoted projection angles, and the absorption data or projection data sets gathered in this manner are used as the basis for calculating 3D image data sets or slice image data sets via appropriate reconstruction methods. The 3D image data sets generally comprise a plurality of slice images, i.e. substantially two-dimensional image data sets, of the patient at a particular z position in the measurement region. A slice image generally reproduces an axial slice of the patient in the measurement region along the extent in the z direction, i.e. along a z axis. What is known as a filtered backprojection (FBP) method is today used for reconstructing images from projection data sets which have been acquired by such a system.

In order to enable the reconstruction of patient anatomy of relevance to irradiation planning, in particular the pulmonary or abdominal carcinoma, in a specific respiratory phase of the patient, the patient's respiratory movement can be acquired during the imaging examination. Preferably, the slice images for each z position of the measurement region can be reconstructed across all the respiratory phases of a respiratory cycle, which in particular reproduces a patient's inhalation and exhalation and corresponds to a periodic segment of the respiratory movement. In this way, it is possible to generate time-resolved image data sets or respiration-correlated series of images which represent the measurement region in a time-resolved manner with regard to a respiratory movement, i.e. substantially at different points in time during the patient's respiratory cycle. As a result, it is possible to ensure particularly suitable adaptation of the dose distribution to a moving planning target volume.

Ideally, the highest possible temporal resolution of the time-resolved image data set is desirable in order to reproduce a movement as precisely as possible. The maximum possible temporal resolution is therefore conventionally selected for data capture and generation of an image data set.

However, on the other hand, selecting the highest possible temporal resolution while simultaneously requiring high image quality, for example with regard to image noise, may result in a higher dose to be administered to a patient or be associated with greater demands on the X-ray sources used and their performance reserves or with limitations on the maximum possible extent of a measurement region or on the duration of measurement data capture.

At the same time, a patient's respiratory movement is highly patient-specific. This means that the same setting parameters for data capture via a medical imaging device are not optimal for each patient, in particular taking account of the countervailing constraints applying to the generated image data sets or to data capture.

SUMMARY

At least one embodiment of the invention enables a medical imaging device for generating image data sets of a patient's measurement region affected by respiratory movement to be actuated in a manner individually matched to the patient.

Further advantageous and in part per se inventive embodiments and further developments of the invention are described in the claims and the following description.

At least one embodiment of the invention relates to a method for actuating a medical imaging device for generating an image data set of a patient's measurement region affected by respiratory movement comprising at least one z position, wherein the image data set comprises at least one slice image data set for the at least one z position. The method comprises at least the steps of provision, automatic derivation and actuation.

In at least one embodiment, the medical imaging device is configured for relative rotational movement between a radiation source comprised by the medical imaging device, in particular an X-ray source, and the patient. The medical imaging device in particular comprises a detector for acquiring radiation, in particular X-rays, emitted by the radiation source, wherein the measurement region of the patient is positioned between the radiation source and the X-ray detector. During the rotational movement, projection data sets are acquired from various projection angles via the detector positioned opposite the radiation source. With the assistance of the projection data sets, an image data set may then be reconstructed for example via a filtered backprojection method or other suitable reconstruction algorithm. A medical imaging device may in particular for example be configured as a computed tomography device.

An embodiment of the invention furthermore relates to a training method for providing a trained function for application in a previously described method. The training method comprises the step of providing a first training respiratory curve of a training patient and a comparison measurement parameter linked therewith via a training interface, wherein comparison measurement parameter determines a temporal resolution of a training slice image data set comprised by a training image data set of a measurement region affected by respiratory movement of a training patient for at least one z position comprised by the measurement region when, with application of the comparison measurement parameter, the training image data set is generated via a training imaging device, and the training slice image data set is based on a plurality of training projection data sets from various projection angles with relative rotational movement between a radiation source of the training imaging device and the training patient.

An embodiment of the invention furthermore relates to an apparatus for actuating a medical imaging device for generating an image data set of a patient's measurement region affected by respiratory movement comprising at least one z position, wherein the image data set comprises at least one slice image data set for the at least one z position.

An embodiment of the invention furthermore relates to a medical imaging device comprising an apparatus for actuating a medical imaging device.

An embodiment of the invention further relates to a training apparatus for providing a trained function for application in a previously described method for actuating a medical imaging device.

An embodiment of the invention furthermore relates to a computer program product with a computer program, which is directly loadable into a storage device of an apparatus for actuating a medical device, with program parts for carrying out all the steps of an embodiment of one of the previously described methods for actuating a medical imaging device when the program parts are run by the apparatus.

An embodiment of the invention furthermore relates to a computer program product with a computer program, which is directly loadable into a training storage device of a training apparatus, with program parts for carrying out all the steps of an embodiment of the previously described training method when the program parts are run by the training apparatus.

An embodiment of the invention may relate to a computer-readable storage medium on which program parts readable and runnable by the apparatus are stored in order to carry out all the steps of a embodiment of the method for actuating a medical imaging device or the aspects thereof when the program parts are run by the apparatus.

Examples of a computer-readable data storage medium are a DVD, a magnetic tape, a hard disk or a USB stick on which electronically readable control information, in particular software, is stored.

An embodiment of the invention may relate to a computer-readable storage medium on which program parts readable and runnable by a training apparatus are stored in order to carry out all the steps of an embodiment of the training method or one of the aspects thereof when the program parts are run by the training apparatus.

An embodiment of the invention may moreover relate to a computer program or computer-readable storage medium comprising a trained function which is provided via an embodiment of the training method for providing a trained function or one of the aspects thereof.

An embodiment of the invention may moreover relate to a method for actuating a medical imaging device for generating an image data set of a measurement region of a patient affected by respiratory movement including at least one z position, the image data set including at least one slice image data set for the at least one z position, the method comprising:

provisioning, via a first interface, a respiratory curve of the patient, the respiratory curve describing the respiratory movement of the patient over at least one respiratory cycle;

automatically deriving at least one measurement parameter, via a computing device, based upon the respiratory curve, the at least one measurement parameter derived determining a temporal resolution of the at least one slice image data set; and actuating, via a controller, the medical imaging device to generate the image data set based upon the at least one measurement parameter automatically derived, wherein, for the at least one z position, a plurality of projection data sets from various projection angles are acquired with relative rotational movements between a radiation source of the medical device and the patient and, wherein the at least one slice image data set of the image data set is generated based upon the plurality of projection data sets acquired.

An embodiment of the invention may moreover relate to a training method for providing a trained function, comprising:

provisioning, via a training interface, a training respiratory curve of a training patient and a comparison measurement parameter linked to the training respiratory curve of the training patient, the comparison measurement parameter determining a temporal resolution of a training slice image data set comprised by a training image data set of a measurement region affected by respiratory movement of the training patient for at least one z position comprised by the measurement region, the training slice image data set being generated, via a training imaging device, upon application of the comparison measurement parameter, and the training slice image data set being based on a plurality of training projection data sets from various projection angles with relative rotational movement between a radiation source of the training imaging device and the training patient;

applying, via a training computing device, the trained function to the training respiratory curve to derive a training measurement parameter;

adapting at least one parameter of the trained function, via the training computing device, based upon a comparison of the training measurement parameter derived and a corresponding comparison measurement parameter; and providing the trained function via a second training interface.

An embodiment of the invention may moreover relate to an apparatus for actuating a medical imaging device for generating an image data set of a measurement region of a patient affected by respiratory movement including at least one z position, the image data set including at least one slice image data set for the at least one z position, the apparatus comprising:

an interface configured to provide at least one respiratory curve of the patient, the at least one respiratory curve describing respiratory movement of the patient over at least one respiratory cycle;

a computing device configured to automatically derive at least one measurement parameter based upon the at least one respiratory curve, the at least one measurement parameter automatically derived determining a temporal resolution of the at least one slice image data set; and a controller configured to actuate the medical imaging device to generate the image data set based upon the at least one measurement parameter automatically derived, wherein, for the at least one z position, a plurality of projection data sets from various projection angles are acquired with relative rotational movement between a radiation source of the medical device and the patient and, based upon the plurality of projection data sets acquired, the at least one slice image data set of the image data set is generated.

An embodiment of the invention may moreover relate to a training apparatus for providing a trained function for application, comprising:

a first training interface configured to provide a training respiratory curve of a training patient and a comparison measurement parameter linked with the training respiratory curve of the training patient, the comparison measurement parameter determining a temporal resolution of a training slice image data set comprised by a training image data set of a measurement region affected by respiratory movement of the training patient for at least one z position comprised by the measurement region, the training image data set being generated via a training imaging device upon application of the comparison measurement parameter and the training slice image data set being based on a plurality of training projection data sets from various projection angles with relative rotational movement between a radiation source of the training imaging device and the training patient;

a training computing device configured to apply a trained function to the first training respiratory curve to derive a training measurement parameter, and further configured to adapt at least one parameter of the trained function based upon a comparison of the training measurement parameter derived and a corresponding comparison measurement parameter; and a second training interface configured to provide the trained function.

An embodiment of the invention may moreover relate to a non-transitory computer program product storing a computer program, directly loadable into a storage device of an apparatus for actuating a medical device, including program parts to carry the method of an embodiment when the program parts are run by the apparatus.

An embodiment of the invention may moreover relate to a non-transitory computer program product storing a computer program, directly loadable into a training storage device of a training apparatus, including program parts for carrying out the method of an embodiment when the program parts are run by the training apparatus.

BRIEF DESCRIPTION OF THE DRAWINGS

The invention is explained below with reference to example embodiments and to the appended figures. The representation in the figures is schematic, highly simplified and not necessarily true to scale. In the figures:

FIG. 2 shows a schematic flow chart for a method for actuating a medical imaging device for generating an image data set,
FIG. 3 and FIG. 4 in each case show an example respiratory curve of a patient.

DETAILED DESCRIPTION OF THE EXAMPLE EMBODIMENTS

Figure 1:
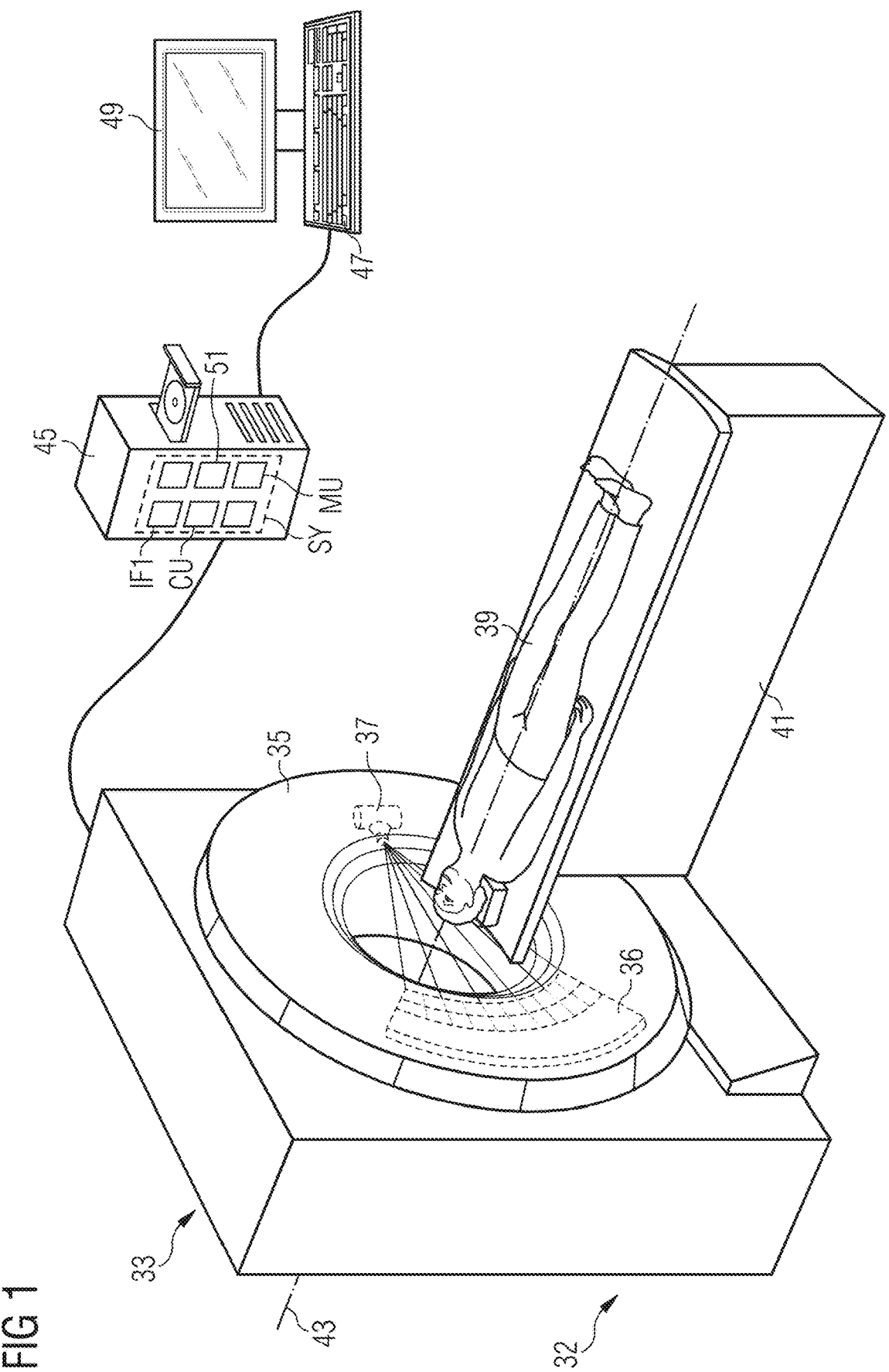
FIG. 1 shows an example medical imaging device.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewritable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewritable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewritable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewritable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for actuating a medical imaging device for generating an image data set of a patient's measurement region affected by respiratory movement comprising at least one z position, wherein the image data set comprises at least one slice image data set for the at least one z position. The method comprises at least the steps of provision, automatic derivation and actuation.

In the provision step, a respiratory curve of the patient which describes the patient's respiratory movement over at least one respiratory cycle is provided via a first interface.

In the automatic derivation step, at least one measurement parameter is automatically derived via a computing unit based upon the provided respiratory curve, wherein the derived measurement parameter determines a temporal resolution of the at least one slice image data set.

In the actuation step, the medical imaging device for generating the image data set based upon the automatically derived measurement parameter is actuated via a control unit, wherein, for the at least one z position, a plurality of projection data sets from various projection angles are acquired with relative rotational movement between a radiation source of the medical device and the patient and, on this basis, the at least one slice image data set of the image data set is generated.

In at least one embodiment, the medical imaging device is configured for relative rotational movement between a radiation source comprised by the medical imaging device, in particular an X-ray source, and the patient. The medical imaging device in particular comprises a detector for acquiring radiation, in particular X-rays, emitted by the radiation source, wherein the measurement region of the patient is positioned between the radiation source and the X-ray detector. During the rotational movement, projection data sets are acquired from various projection angles via the detector positioned opposite the radiation source. With the assistance of the projection data sets, an image data set may then be reconstructed for example via a filtered backprojection method or other suitable reconstruction algorithm. A medical imaging device may in particular for example be configured as a computed tomography device.

A measurement region may in particular extend along a z axis or comprise at least one z position along the z axis. The z axis may in particular run along a longitudinal axis extending in the longitudinal direction of the patient. The longitudinal axis of the patient may moreover be parallel to a longitudinal axis extending in the longitudinal direction of a patient couch. The measurement region may include the at least one z position, wherein the at least one z position describes a position along the z axis of a patient slice to be reproduced. A slice image data set for the at least one z position may in particular reproduce the slice of the patient at the at least one z position. An axis of rotation of a computed tomography device conventionally corresponds to the longitudinal axis of a patient couch and the z axis.

A slice image data set, i.e. the image data for a z position, may in particular have a slice thickness with an extent in the z direction. A minimum slice thickness may for example be determined by a pixel size of a detector which is used.

A plurality of projection data sets from a, preferably contiguous, angular range of the rotational movement of the radiation source may be assigned to the slice image data set, based upon which the slice image data set can be reconstructed. This angular range may be denoted projection angle range. Ideally, the projection angle range encompasses at least 180°, which is conventionally a minimum for the reconstruction of a slice image data set. The larger the projection angle range, the more projection data sets with the at least one angle within the projection angle range are used in reconstructing a slice image data set. If the projection angle range amounts to at least 180°, it is conventionally possible to minimize image artifacts in the slice image which are in particular caused by a projection angle range of less than 180°.

The projection data sets can be captured via a computed tomography device by way of helical acquisition. The patient is here continuously pushed through a maximum visual field of the computed tomography device. Alternatively to helical acquisition, the patient couch may be pushed in discrete steps through the maximum visual field of the computed tomograph. In helical acquisition, the "pitch" which describes table advance is proportional to a table advance of the patient couch and an extent of the X-ray detector in the z direction of the computed tomograph. Typical pitch values during performance of a measurement in a computed tomograph are above 0 and below 2. When capturing moving structures, i.e. for example a measurement region affected by respiratory movement, a small pitch, for example of less than 1, and/or a short rotation cycle time of the radiation source is used. The rotation cycle time describes the time interval which is required for a complete revolution of the radiation source around the patient. The shorter is the rotation cycle time of the radiation source during rotational movement, the greater is the radiation source/detector velocity and the faster in particular the radiation source and the detector rotate around the patient and/or the more projection data sets can be acquired per unit time. Conventionally, in particular the at least one radiation source and the at least one X-ray detector rotate continuously during the imaging examination.

During capture of the projection data sets, it is conventional to store an angle at which the at least one radiation source and the at least one X-ray detector are located relative to the patient couch or the patient during acquisition of the projection data sets, and a current z position of the patient couch for example with reference to the projection data.

For the purposes of the invention, the temporal resolution of a slice image data set should be taken to mean that the temporal resolution reflects the time interval which elapses during acquisition of the projection data sets for a slice image data set. The shorter is the time interval, i.e. the better is the temporal resolution, the less will a patient have moved during acquisition and the less affected will be the slice image data set by movement in the measurement region, i.e. by movement artifacts, and the sharper will it be possible to reproduce moving structures in the slice image data set. If, moreover, for a sequence of points in time, i.e. for a plurality of points in time, a slice image data set is in each case comprised for the at least one z position, i.e. a time-resolved image data set is acquired, the temporal resolution determines the minimum time interval between two temporally successive slice image data sets. The temporal resolution in particular defines a maximum temporal coherence of patient structures moved by the respiratory movement, for example of a skin surface, an organ, a carcinoma and/or a tumor. If the temporal resolution comprises N seconds, the projection data sets at the at least one z position according to the projection angle range are preferably acquired within N seconds. Maximum temporal coherence may be dependent on other kinds of patient movement. Maximum temporal coherence during the imaging examination may in particular be optimized if there is no movement, in particular of the structures moved by respiratory movement. In other words, the less patient movement there is, the better is the maximum temporal coherence.

Temporal resolution may in particular be dependent on the rotation cycle time and on the projection angle range which is used. Temporal resolution may in particular be directly proportional to the product of the rotation cycle time and the projection angle range.

A maximum temporal resolution is conventionally selected for time-resolved measurements, for example by selecting the shortest possible rotation cycle time and the possible projection angle range on which a slice image data set is based in order to reproduce tumors and organs at risk as accurately as possible.

The inventor has however recognized that a maximum temporal resolution is not necessarily always required for an optimum portrayal. The inventor has recognized that a patient's respiratory movement, i.e. for example the extent of movement per unit time, is highly patient-specific and may moreover optionally be affected by current constraints, such that it may not always be productive always to select the highest possible temporal resolution but may instead be advantageous to select a temporal resolution which is suitable for the current patient. In this manner, it is advantageously possible to avoid administering an unnecessary high dose or to avoid restrictions with regard to the scanning procedure.

According to an embodiment of the invention, at least one measurement parameter is automatically derived based upon a provided respiratory curve of the patient, wherein the derived measurement parameter determines a temporal resolution of the at least one slice image data set. In other words, a temporal resolution specific to the individual patient which is based on the respiratory curve is used to generate the image data set using the measurement parameter. The measurement parameter is preferably derived based upon a currently prevailing respiratory curve, i.e. has been recorded close in time to the imaging examination.

A respiratory curve of a patient which reflects the patient's respiratory movement may be acquired for example via a sensor, for example via a camera or a respiration belt. The respiratory movement conventionally describes free respiration by the patient and in particular comprises at least one respiratory cycle of the patient. The respiratory movement is in particular acquired over at least one complete respiratory cycle of the patient, wherein the entire respiratory cycle comprises at least a single inhalation and a single exhalation of the patient. The provided respiratory curve preferably comprises more than one respiratory cycle. The respiratory cycle preferably corresponds to a periodic segment of the respiratory movement. The duration of the periodic segment corresponds to the duration of the respiratory cycle. The duration of a respiratory cycle or an average duration of a plurality of successive respiratory cycles and thus a respiratory rate, i.e. for example a number of inhalations or exhalations per unit time can be determined from the respiratory curve. The slower the patient breathes, the higher is respiratory rate.

The profile of a patient's respiratory curve may in particular be individual to the patient, i.e. the gradients arising, the duration of an inhalation or exhalation, or the occurrence of intermediate resting phases with little or no movement can differ from patient to patient and possibly also from imaging examination to imaging examination of a patient. This may in particular also be derivable independently of a patient's (average) respiratory rate or at least not be straightforwardly derivable from a patient's (average) respiratory rate.

Provision of a respiratory curve via the first interface may involve reading out the data from a storage unit on which a respiratory curve of the patient which has been acquired via a sensor is stored. Provision may involve receiving measurement points of the respiratory curve from a sensor unit configured to acquire a patient's respiratory curve.

In particular, no user interaction is necessary for automatic derivation of the at least one measurement parameter. As a result, it is possible to avoid incorrectly defining the at least one measurement parameter. Automatic derivation in particular proceeds in a computing unit. For this purpose, the computing unit advantageously has a storage device onto which program code means are loadable. The program code means in particular include program code which enables automatic derivation of the at least one measurement parameter when a patient's respiratory curve is provided.

Automatic derivation is particularly advantageous because the at least one measurement parameter for the provided respiratory curve and thus for each patient is automatically individually calculated and generation of the image data set is thus particularly suitably adapted to the patient because the at least one measurement parameter is not selected from predetermined parameter sets averaged over a patient group or with the assistance of simplified correlations which may be correct at most on average.

Automatic derivation may involve deriving more than just one measurement parameter.

Automatic derivation may involve the application of a trained function, wherein the patient's respiratory curve or parameters derived therefrom enter into the trained function as input parameters. Automatic derivation may involve an analysis of the respiratory curve which analyzes the respiratory curve with regard to its profile in order to extract at least one value, preferably a plurality of values, relating to a duration or gradient of an inhalation phase or an exhalation phase or a duration of a resting phase of the respiratory movement based upon the provided respiratory curve. These values may be used as input parameters for a trained function or also for querying a plurality of measurement parameters stored in a database which are linked with the input parameters.

By establishing the measurement parameter for an individual patient, it is advantageously possible to avoid an unnecessarily high administered dose with regard to temporal resolution or unnecessary restrictions with regard to a scan range or duration. A higher temporal resolution generally also means a higher dose for the patient at otherwise constant image quality (for example with regard to image noise). Because acquiring a projection data set takes less time and/or fewer projection data sets contribute to generating the slice image data set, this has to be compensated by a higher administered dose. A higher temporal resolution generally also means greater demands being placed on the X-ray tubes and their performance reserves. This may lead to restrictions in terms of scan range or duration, for example for obese patients for whom a higher tube current has to be set in order to be able to achieve the required image quality. If, for example, a minimum rotation cycle time or a small number of projection data sets contributing to a slice image data set for a point in time is simultaneously selected, wherein the intention is simultaneously to ensure constant image quality, the radiation sources used may come up against their performance limits.

For example, a greater temporal resolution can be selected for a slow breathing patient who has long inhalation phases or exhalation phases with a moderate gradient since in this case there is slower movement occurring in the measurement region. On the other hand, in a patient with very steep rises on inhalation or exhalation, a higher temporal resolution must be selected in order to generate a slice image data set with sufficient temporal coherence. There may here be a non-trivial correlation between respiration and the measurement parameters to be selected. Simply making a link, for example, with an average respiratory rate may provide unsatisfactory results here. Automatic derivation taking account of a patient's respiratory curve, in contrast, may enable a suitable selection to be made in particular also by less highly trained personnel and make an overall contribution to time-efficient generation of image data sets, wherein errors and consequential inadequate image quality or an unnecessarily administered dose can be avoided.

Based upon the automatically derived measurement parameters, the medical imaging device is actuated to generate the image data set comprising the at least one slice image data set. A plurality of projection data sets from various projection angles with relative rotational movement between a radiation source of the medical imaging device and the patient are here acquired for the at least one z position and, on this basis, the slice image data set is generated.

Actuation may relate to the acquisition of the projection data sets via the medical imaging device per se or also to reconstruction of the image data set based upon the acquired projection data sets.

According to one method variant, the automatically derived measurement parameter comprises at least one rotation cycle time of the radiation source during the relative rotational movement and/or a projection angle range which comprises the angular range of the projection angles, on which the at least one slice image data set is based. Automatic derivation may also comprise derivation both of the rotation cycle time and of the projection angle range. A defined correlation between the rotation cycle time and the projection angle range may also be determined, such that once one measurement parameter has been automatically derived, the other measurement parameter is likewise also determined.

Advantageously, it is possible to determine a temporal resolution which is matched to a patient and their respiratory movement.

Actuation may then in particular comprise actuation of the radiation source-detector unit for acquisition, in particular the velocity of the rotational movement, i.e. the rotation cycle time. Actuation may then involve selection, based upon the projection angle range, of the acquired projection data sets which enter into the generation of the at least one tomographic image data set.

Further measurement parameters may also be derived based upon the automatically derived measurement parameter(s) relating to temporal resolution. Actuation may accordingly also relate to further parameters. For example, further setting parameters may depend on an automatically derived measurement parameter relating to temporal resolution or be linked with an automatically derived measurement parameter. This may for instance comprise a tube current which is used of an X-ray tube used as radiation source or the table advance, for example the pitch in a helical scan. A defined correlation, for example in the form of a mathematical function, may be predetermined between the measurement parameters. Automatic derivation may also comprise derivation of a defined set of interlinked measurement parameters, the set comprising more measurement parameters than the at least one measurement parameter which determines the temporal resolution.

According to one variant of the method, a dose parameter and/or a performance parameter of the radiation source are moreover in particular involved in the automatic derivation.

A performance parameter of the radiation source may for example relate to a maximum tube power of an X-ray tube which is used. When a very high temporal resolution is used while high image quality is also desired, in particular in conjunction with large volumes to be penetrated, it may be necessary to use a higher tube current. If the intention is moreover to generate a plurality of slice image data sets, for instance when scanning an extended measurement region and/or over a long duration, it may happen that performance limits of the radiation source which is used are reached, so limiting a maximum scannable measurement region or a maximum scan duration. In this case, a selected lower temporal resolution matching a patient-specific respiratory curve may be advantageous. This is advantageously taken into account during automatic derivation of a measurement parameter relating to temporal resolution.

A dose parameter may in particular affect image quality, for example with regard to image noise. At the same time, any unnecessary exposure of a patient to radiation is to be avoided. Selecting an unnecessarily high temporal resolution may lead to an unnecessarily high administered dose. In particular, automatic derivation may enable improved selection of dose/image quality and temporal resolution. A possibly less highly trained user may not be aware of the non-trivial correlations between respiration, image quality, dose and tube power. Automatic derivation taking account of the prevailing constraints may advantageously assist in avoiding an incorrect or suboptimal selection of parameters.

According to one method variant, automatic derivation comprises applying a trained function, wherein at least one parameter of the trained function is adapted to a comparison between a training measurement parameter derived from a training respiratory curve of a training patient and a comparison measurement parameter, wherein the training respiratory curve and the comparison measurement parameter are linked together.

Derivation using a trained function may advantageously permit particularly time-efficient derivation taking account of the patient-specific respiratory curve.

A trained function may preferably be embodied via an artificial intelligence system, i.e. by a machine learning method. Derivation based upon the application of a trained function allows better account to be taken of all the relevant influencing variables for derivation, including those for which a user, in particular for example also a less highly trained or less experienced user, cannot estimate any correlation with derivation or can do so only with difficulty. An artificial intelligence system may be taken to be a system for artificially generating knowledge from experience. An artificial system learns from examples in a training phase and, once the training phase is complete, is capable of generalizing. Using such a system may involve the recognition of patterns and regularities in the training data. After the training phase, the artificial intelligence system can extract, for example from previously unknown measurement data, features or parameters which enter into the derivation. After the training phase, the optimized, i.e. trained, algorithm can estimate suitable measurement parameters for generating the image data set, for example based upon a previously unknown measured respiratory curve. The artificial intelligence system may be based on an artificial neural network or also on another machine learning method. In particular, after the training phase, a trained function based on an artificial intelligence system can automatically derive the measurement parameter in a particularly reliable and time-efficient manner.

A trained function in particular maps input data onto output data. The output data may here in particular furthermore be dependent on one or more parameters of the trained function. The one or more parameters of the trained function may be determined and/or adapted by training. Determination and/or adaptation of the one or more parameters of the trained function may in particular be based on a pair composed of training input data and associated, i.e. linked, comparison output data, wherein the trained function is applied to the training input data to generate training output data. In particular, determination and/or adaptation may be based on a comparison of the training output data and the training comparison data. In general, a trainable function, i.e. a function with one or more parameters which are not as yet adapted, is also denoted a trained function.

Other terms for trained function are trained mapping rule, mapping rule with trained parameters, function with trained parameters, algorithm based on artificial intelligence or machine learning algorithm. One example of a trained function is an artificial neural network, wherein the edge weights of the artificial neural network correspond to the parameters of the trained function. The term "neural net" may also be used instead of the term "neural network". In particular, a trained function may also be a deep artificial neural network or deep neural network. Another example of a trained function is a "support vector machine" while other machine learning algorithms may furthermore in particular also be used as a trained function.

The trained function may in particular be trained via backpropagation. First of all, training output data can be determined by applying the trained function to the training input data. A deviation between the training output data and the training comparison data may then be established by applying an error function to the training output data and the training comparison data. Furthermore, at least one parameter, in particular a weighting, of the trained function, in particular of the neural network, may be iteratively adapted based upon a gradient of the error function with regard to the at least one parameter of the trained function. As a result, the deviation between the training output data and the training comparison data can advantageously be minimized during the training of the trained function.

The trained function, in particular the neural network, advantageously has an input layer and an output layer. The input layer may here be configured to receive input data. The output layer may furthermore be configured to provide output data. The input layer and/or the output layer may here in each case comprise a plurality of channels, in particular neurons.

According to an embodiment of the invention, the input data for the trained function may comprise a first provided respiratory curve of the patient or a parameter derived therefrom, preferably a plurality of parameters derived therefrom which characterize the profile of the respiratory curve. According to an embodiment of the invention, the output data may in particular comprise the at least one measurement parameter for generating the at least one slice image data set, which parameter relates to the temporal resolution of the slice image data set.

According to an embodiment of the invention, in the training phase of the trained function, a training respiratory curve, preferably a plurality of training respiratory curves, of a training patient, preferably of a plurality of training patients, is/are in particular used as training input data. On this basis, a training measurement parameter can be derived as training output data. Furthermore, at least one parameter of the trained function can be adapted to a comparison of the derived training measurement parameter of the training patient with a comparison measurement parameter of the training patient as training comparison data.

The training input data and the training comparison data are linked together. In particular, it is possible to use annotated training input data which has been annotated, for example by expert knowledge, before the beginning of the training phase, such that training comparison data in relation to the training input data is advantageously available. For example, before a training phase in each case at least one comparison measurement parameter may be assigned to a training respiratory curve. The comparison measurement parameter may determine a suitable temporal resolution. The comparison measurement parameter may for example comprise a rotation cycle time suitable for use with the respective training respiratory curve or a suitable projection angle range. Account may moreover here also be taken of a dose parameter or a tube power parameter. Moreover, account may be taken of an image quality parameter. In particular, the expert knowledge which allows the assignment to be made may be based on experimental experience and experimental studies which were obtained with the assistance of real measurements or simulations before the beginning of a training phase. The input data may be based, for example, on real measurements on real training patients. The input data may be based on simulations or on phantom measurements which can then be annotated.

A trained function can be directly applied to a provided respiratory curve. The respiratory curve may correspond to the input parameters of the trained function. The input parameters of a trained function may, however, also be based on values previously extracted from the respiratory curve.

According to one method variant, automatic derivation comprises extracting the at least one measurement parameter via the computing unit, at least one value relating to a duration or gradient of an inhalation phase or exhalation phase or a duration of a resting phase of the respiratory movement based upon the provided respiratory curve and, on this basis, deriving the measurement parameter. For example, the gradient in a respiratory curve or the profile of a gradient in the respiratory curve may be established with the assistance of mathematical derivations.

Alternatively to using a trained function, an extracted value may also be used in conjunction with a database query. Determination of the at least one measurement parameter based upon the at least one extracted value may comprise querying a measurement parameter database stored in a storage unit, wherein at least one extracted value or a parameter derived therefrom is used as a query parameter for the query.

The one or preferably a plurality of extracted values may be linked with the at least one measurement parameter based upon expert knowledge and experimental experience. In other words, the measurement parameters stored in the measurement parameter database are in each case linked with one or with a group of extracted values for a query. A classification into one respiratory pattern group of a plurality of respiratory pattern groups may also firstly be made based upon preferably a plurality of extracted values. A respiratory pattern group may be assigned to the at least one measurement parameter and for example be present in a measurement parameter database linked with the respiratory pattern group.

Such an implementation can be put into practice without a training phase of a trained function. However, this may amount to a less flexible and less patient-specific implementation than the application of a trained function by the classification or determination of what is merely the greatest possible match with previously defined respiratory patterns or the fixed assignment of parameters via a database.

According to one variant of the method, the generated image data set comprises slice image data sets for a plurality of points in time for the at least one z position. In the step of actuating the medical imaging device for generating the image data set based upon the automatically derived measurement parameter for the at least one z position, in each case a plurality of projection data sets are then acquired from various projection angles for each point in time of the plurality of points in time. The measurement region can advantageously be reproduced in a time-resolved manner at least at the at least one z position and a respiratory movement of the measurement region or a movement of organs or structures in the measurement region caused thereby can be tracked.

According to one method variant, the slice image data sets of the generated image data set reproduce the patient's respiratory cycle over the entire duration of the respiratory cycle. A movement can advantageously be tracked over the entire respiratory cycle and for example taken into account in irradiation planning.

According to one variant of the method, the patient's respiratory movement is additionally acquired in real time during actuation of the medical imaging device and the image data for a point in time of the plurality of points in time is generated according to a respiratory phase of the patient's respiratory movement.

In particular, the respiratory phase can be assigned to at least one of the time-resolved slice image data sets. The at least one of the time-resolved slice image data sets in particular shows the z position according to the respiratory phase. For example, the user can select on the monitor the respiratory phase to be displayed and the slice image data set associated with the respiratory phase can be displayed.

If the measurement region has a 3D volume with an extent in the z direction and the measurement region for example comprises a patient's thorax, the patient's thorax can be displayed on a monitor according to the selected respiratory phase. For example, depending on the user's selection, the patient can be shown once during inhalation and another time during exhalation.

Generation of the image data set of the patient according to the at least one measurement parameter in the measurement region via the medical imaging device may in particular comprise the reconstruction of respiration-correlated images or respiration-correlated series of images.

An embodiment of the invention furthermore relates to a training method for providing a trained function for application in a previously described method. The training method comprises the step of providing a first training respiratory curve of a training patient and a comparison measurement parameter linked therewith via a training interface, wherein the comparison measurement parameter determines a temporal resolution of a training slice image data set comprised by a training image data set of a measurement region affected by respiratory movement of a training patient for at least one z position comprised by the measurement region when, with application of the comparison measurement parameter, the training image data set is generated via a training imaging device, and the training slice image data set is based on a plurality of training projection data sets from various projection angles with relative rotational movement between a radiation source of the training imaging device and the training patient.

The training method furthermore comprises the step of applying the trained function to the provided first training respiratory curve and thus derivation of a training measurement parameter via a training computing unit, and the step of adapting the at least one parameter of the trained function based upon a comparison of the derived training measurement parameter and the corresponding comparison measurement parameter via the training computing unit.

The training method furthermore comprises the step of providing the trained function via a second training interface.

A trained function can advantageously be provided.

The provision of a training respiratory curve and of a training measurement parameter linked therewith may in particular comprise acquiring and/or reading out a computer-readable data storage device and/or receipt from a data storage unit, for example a database. The first training respiratory curve and the comparison measurement parameter may be based on real measurements of a real training patient and measurement parameters assigned thereto. The training respiratory curve may be captured with the assistance of a sensor which is applied to a training patient or via a camera and stored and may thereafter be provided for training. The at least one comparison measurement parameter may be stored linked with the training measurement parameter and then be provided for training. Artificially generated, i.e. simulated, training data sets or training data sets based on phantom measurements may in general also be used.

The training respiratory curve and the comparison measurement parameter linked therewith is preferably based on domain-specific, measured respiratory curves from a real patient population of the medical imaging device or from the same group of devices as the medical device. This means that the respiratory curve used for the training method and the respiratory curve on which basis an automatic derivation is carried out preferably have been or are established under similar conditions.

An embodiment of the invention furthermore relates to an apparatus for actuating a medical imaging device for generating an image data set of a patient's measurement region affected by respiratory movement comprising at least one z position, wherein the image data set comprises at least one slice image data set for the at least one z position.

The apparatus comprises a first interface configured to provide a respiratory curve of the patient, which describes the patient's respiratory movement over at least one respiratory cycle.

The apparatus furthermore comprises a computing unit configured to automatically derive the at least one measurement parameter based upon the provided respiratory curve, wherein the derived measurement parameter determines a temporal resolution of the at least one slice image data set.

The apparatus further comprises a control unit configured to actuate the medical imaging device for generating the image data set based upon the automatically derived measurement parameter, wherein, for the at least one z position, a plurality of projection data sets from various projection angles are acquired with relative rotational movement between a radiation source of the medical device and the patient and, on this basis, the at least one slice image data set of the image data set is generated.

The computing unit or the control unit may be configured to derive, based upon the derived measurement parameter, a control signal for actuation of the medical device, based upon which the medical imaging device can be actuated. In particular, the apparatus can be configured to actuate the medical imaging device automatically based upon the derived measurement parameter.

Such an apparatus for actuating a medical imaging device may in particular be configured to carry out the previously described method according to an embodiment of the invention for actuating a medical imaging device and the aspects thereof. The apparatus may be configured to carry out the method and the aspects thereof by the interface, the computing unit and the control unit being configured to carry out the corresponding method steps.

The advantages of the proposed apparatus substantially correspond to the advantages of the proposed method for actuating a medical device. Features, advantages or alternative embodiments mentioned in this connection are likewise also applicable to the apparatus for actuation and vice versa.

An embodiment of the invention furthermore relates to a medical imaging device comprising an apparatus for actuating a medical imaging device.

The medical imaging device is here advantageously configured to carry out an embodiment of the proposed method for actuating the medical imaging device. The advantages of the proposed medical imaging device substantially correspond to the advantages of the proposed method for actuating a medical device. Features, advantages or alternative embodiments mentioned in this connection are likewise also applicable to the medical imaging device and vice versa.

The medical imaging device in particular comprises a radiation source and, positioned opposite thereto, a detector. The patient may be positioned between the radiation source, for example an X-ray tube, and the X-ray detector. An appropriate patient couch may be provided for this purpose. The medical imaging device is configured to acquire a plurality of projection data sets from various projection angles with relative rotational movement between the radiation source and the patient. The medical imaging device may preferably be configured as a computed tomography device. The medical imaging device may, however, also be configured for example as a C-arm X-ray device and/or Dyna-CT or the like.

The medical imaging device may advantageously be actuated based upon the derived measurement parameter.

An embodiment of the invention further relates to a training apparatus for providing a trained function for application in a previously described method for actuating a medical imaging device.

The training apparatus comprises a first training interface configured to provide a training respiratory curve of a training patient and a comparison measurement parameter linked therewith via a training interface. The comparison measurement parameter here determines a temporal resolution of a training slice image data set comprised by a training image data set of a measurement region affected by respiratory movement of a training patient for at least one z position comprised by the measurement region when, with application of the comparison measurement parameter, the training image data set is generated via a training imaging device. The training slice image data set is here based on a plurality of training projection data sets from various projection angles with relative rotational movement between a radiation source of the training imaging device and the training patient.

The training apparatus furthermore comprises a training computing unit configured to apply a trained function to the first training respiratory curve and so derive a training measurement parameter.

The training computing unit is furthermore configured to adapt at least one parameter of the trained function based upon a comparison of the derived training measurement parameter and the corresponding comparison measurement parameter.

The training apparatus furthermore comprises a second training interface which is configured to provide the trained function.

Such a training apparatus may in particular be configured to carry out the previously described training method for providing a trained function and the aspects thereof. The training apparatus is configured to carry out this method and the aspects thereof by the training interface and the training computing unit being configured to carry out the corresponding method steps.

An embodiment of the invention furthermore relates to a computer program product with a computer program, which is directly loadable into a storage device of an apparatus for actuating a medical device, with program parts for carrying out all the steps of an embodiment of one of the previously described methods for actuating a medical imaging device when the program parts are run by the apparatus.

An embodiment of the invention furthermore relates to a computer program product with a computer program, which is directly loadable into a training storage device of a training apparatus, with program parts for carrying out all the steps of an embodiment of the previously described training method when the program parts are run by the training apparatus.

A computer program product may be a computer program or comprise a computer program. As a consequence, the method according to an embodiment of the invention can be carried out quickly, identically repeatably and robustly. The computer program product is configured such that it can carry out the method steps according to an embodiment of the invention via the apparatus or training apparatus. The apparatus or training apparatus must here in each case have the prerequisites such as for example an appropriate working memory, an appropriate graphics card or an appropriate logic unit for it to be possible to carry out the respective method steps efficiently. The computer program product is for example stored on a computer-readable medium or stored on a network or server from which it can be loaded into a computing unit or training computing unit of the apparatus or training apparatus.

An embodiment of the invention may relate to a computer-readable storage medium on which program parts readable and runnable by the apparatus are stored in order to carry out all the steps of a embodiment of the method for actuating a medical imaging device or the aspects thereof when the program parts are run by the apparatus.

Examples of a computer-readable data storage medium are a DVD, a magnetic tape, a hard disk or a USB stick on which electronically readable control information, in particular software, is stored.

An embodiment of the invention may relate to a computer-readable storage medium on which program parts readable and runnable by a training apparatus are stored in order to carry out all the steps of an embodiment of the training method or one of the aspects thereof when the program parts are run by the training apparatus.

An embodiment of the invention may moreover relate to a computer program or computer-readable storage medium comprising a trained function which is provided via an embodiment of the training method for providing a trained function or one of the aspects thereof.

An implementation largely through software has the advantage that processing units and/or training apparatuses which are already in service can also straightforwardly be retrofitted to operate in the manner according to an embodiment of the invention via a software update. In addition to the computer program, a computer program product may comprise additional elements such as for example documentation and/or additional components, as well as hardware components, such as for example hardware keys (dongles etc.) for using the software.

For the purposes of the invention, features which are described in relation to different embodiments of the invention and/or different categories of claim (method, use, apparatus, system, arrangement etc.) may be combined to yield further embodiments of the invention. For example, a claim relating to an apparatus may also be developed with features which are described or claimed in connection with a method and vice versa. Functional features of a method may in this case be embodied by appropriately configured physical components.

Use of the indefinite article "a" or "an" does not rule out the possibility of the feature in question also being present in multiple instances. Use of the term "include" does not rule out the possibility of the terms linked by the term "include" being identical. For example, the medical imaging apparatus includes the medical imaging apparatus. Use of the term "unit" does not rule out the possibility of the object to which the term "unit" relates including a plurality of components which are spatially separated from one another.

The expression "based upon" may be understood, in the context of the present application, in particular to mean "using". In particular, wording according to which a first feature is generated (or: established, determined etc.) based upon a second feature does not rule out the possibility of the first feature being generated (or: established, determined etc.) based upon a third feature.

FIG. 1 shows a medical imaging device 32 in the form of a computed tomography device.

The computed tomography device has a gantry 33 with a rotor 35. The rotor 35 comprises at least one radiation source 37, in particular an X-ray tube, and, positioned opposite thereto, at least one detector 36. The detector 36 and the radiation source 37 are rotatable about a common axis 43 (also denoted axis of rotation). The patient 39 is placed on a patient couch 41 and can be moved along the axis of rotation 43 through the gantry 33. The patient 39 may in general comprise for example an animal patient and/or a human patient.

The computed tomography device 32 comprises a processing unit 45 comprising an apparatus SY for actuating the medical imaging device 32 with a computing unit CU, an interface IF1 and a control unit 51. The processing unit moreover comprises a storage unit MU.

An input facility 47 and an output facility 49 are furthermore connected to the processing unit 45. The input facility 47 and the output facility 49 may for example enable user interaction, for example manual configuration, confirmation or initiation of a method step. For example, computed tomograph projection data sets and/or a slice image data set or a three-dimensional image data set may be displayed to the user on the output apparatus 49 comprising a monitor.

Conventionally, a plurality of (raw) projection data sets of the patient 32 are captured from a plurality of projection angles during relative rotational movement between the radiation source and the patient while the patient 39 is moved continuously or sequentially through the gantry 33 via the patient couch 41.

Then, based upon the projection data sets, a slice image data set for a respective z position along the axis of rotation within a measurement region can be reconstructed via a mathematical method, for example comprising filtered backprojection or an iterative reconstruction method. Projection data sets from a projection angle range, on which the slice image data set is based, are assigned to each slice image data set.

The apparatus comprised by the processing unit 45 for actuating the medical imaging device is in particular configured to carry out a method according to an embodiment of the invention for actuating the medical imaging device 32 for generating an image data set of a patient's 39 measurement region affected by respiratory movement comprising at least one z position, wherein the image data set comprises at least one slice image data set for the at least one z position.

FIG. 2 shows an example flow chart of such a method for actuating a medical imaging device.

In provision step ST1, a respiratory curve S of the patient 39 which describes the patient's 39 respiratory movement over at least one respiratory cycle is provided via a first interface IF1.

In automatic derivation step ST2, at least one measurement parameter is derived via a computing unit CU based upon the provided respiratory curve S, wherein the derived measurement parameter determines a temporal resolution of the at least one slice image data set.

In actuation step ST3, the medical imaging device 32 for generating the image data set based upon the automatically derived measurement parameter is actuated via a control unit 51, wherein, for the at least one z position, a plurality of projection data sets from various projection angles are acquired with relative rotational movement between a radiation source 37 of the medical device 32 and the patient 39 and, on this basis, the at least one slice image data set of the image data set is generated.

The method may moreover comprise step ST4 of providing the at least one slice image data set.

The method may moreover comprise acquisition ST0 of a respiratory curve S of the patient, which is then provided via the interface for automatic derivation.

FIG. 3 and FIG. 4 show two example respiratory curves S over time t. The respiratory curves S(t) shown extend over a plurality of respiratory cycles TC, in the case of FIG. 3 over three complete respiratory cycles TC, 1, TC, 2 and TC, 3, in each case at least including an exhalation phase TE, 1, TE, 2 and TE, 3 and an inhalation phase TI, 1, TI, 2 and TI, 3. In the case of FIG. 4, substantially two complete respiratory cycles TC, 1, TC, 2 are acquired. The respiratory curve S(t) of FIG. 4 moreover includes a relatively long resting phase TR, 1, TR, 2 between a respective exhalation and inhalation in which virtually no respiratory movement is visible.

On the assumption that the period of time over which the indicated curves S(t) extend is similar or identical, example respiratory curve S(t) of FIG. 3 can be assigned a distinctly higher respiratory rate than FIG. 2. At the same time, because the cycles do not have long resting phases, the average gradient during an inhalation or exhalation is nevertheless moderate.

In contrast, at a comparatively low respiratory rate, the respiratory curve S(t) of FIG. 4 shows pronounced resting phases, for which reason the average gradient during an inhalation and exhalation is, however, very steep in relation to the very low respiratory rate.

In this indicated case, it would be appropriate to select a high temporal resolution of the slice image data set in order to generate a high quality image data set which in particular includes few movement artifacts, although the respiratory rate is very low. In the case of FIG. 3, on the other hand, a comparatively lower temporal resolution would be sufficient.

Taking account of patient-specific respiratory patterns for defining a temporal resolution enables optimum adaptation to the prevailing constraints due to the patient. Automatic derivation in particular also makes it possible to take account of non-trivial correlations in a time-efficient manner and while avoiding incorrect settings.

Temporal resolution may in particular be dependent on a rotation cycle time and on the projection angle range which is used. Temporal resolution may in particular be directly proportional to the product of the rotation cycle time and the projection angle range. According to one method variant, the automatically derived measurement parameter comprises at least one rotation cycle time of the radiation source 37 during the relative rotational movement and/or a projection angle range which comprises the angular range of the projection angles, on which the at least one slice image data set is based. Automatic derivation may also comprise derivation both of the rotation cycle time and of the projection angle range. A defined correlation between the rotation cycle time and the projection angle range may also be determined, such that once one measurement parameter has been automatically derived, the other measurement parameter is likewise also determined. Further parameters may also enter into such a defined correlation.

Further measurement parameters may also be derived or calculated based upon the automatically derived measurement parameter(s) relating to temporal resolution. Actuation may accordingly also relate to further parameters. For example, further setting parameters may depend on an automatically derived measurement parameter relating to temporal resolution or at least be linked therewith. This may for instance comprise a tube current which is used of an X-ray tube used as radiation source or the table advance, for example the pitch in a helical scan. For instance, at a higher rotation cycle time it is optionally possible to select a higher pitch. If, for example, the at least one z position is to be reproduced over an entire respiratory cycle, pitch may be dependent on a ratio of rotation cycle time and duration of a respiratory cycle. If image quality per reconstructed slice image data set, for example defined by way of a slice-effective tube current-time product, is to be kept constant, tube current can be reduced at a reduced rotation cycle time. The slice-effective tube current-time product in particular provides a measure of an emitted amount of X-rays and is typically proportional to radiation exposure. Conventionally, the higher is the slice-effective tube current-time product, the higher is radiation exposure. The slice-effective tube current-time product may in particular correspond to a product of the tube current of the computed tomography device during the imaging examination and the tube rotation cycle time used during the imaging examination. Equally, a lower tube current is likewise possible with a larger projection angle range in order to maintain constant image quality.

Preferably, automatic derivation comprises applying a trained function, wherein at least one parameter of the trained function is adapted to a comparison between a training measurement parameter derived from a training respiratory curve of a training patient and a comparison measurement parameter, wherein the training respiratory curve and the comparison measurement parameter are linked together. The trained function preferably comprises a neural network.

The method may also comprise that derivation ST2 of the at least one measurement parameter via the computing unit CU comprises extracting at least one value relating to a duration of an exhalation phase TE, 1, TE, 2, TE, 3 or inhalation phase TI, 1, TI, 2, TI, 3 or gradient of an inhalation phase or exhalation phase or a duration of a resting phase TR, 1, TR, 2 of the respiratory movement based upon the provided respiratory curve S and, on this basis, deriving the measurement parameter.

Determination of the one measurement parameter based upon the extracted value may comprise querying a measurement parameter database stored in a storage unit MU, wherein at least one extracted value or a parameter derived therefrom is used as a query parameter for the query.

Preferably, a dose parameter or a performance parameter of the radiation source 37 moreover enters into the automatic derivation step ST2. In particular, account may be taken of a dose parameter or a performance parameter during automatic derivation ST2.

For example, account may be taken of a dose parameter or a performance parameter in an annotation of training comparison data which is then used for training a trained function. For example, account may be taken of a dose parameter or a performance parameter in the provision of a measurement parameter database. A dose parameter or a performance parameter may enter into a derivation as a constraint. A dose parameter may for example relate to a maximum total dose for the generation of the image data set, a slice-effective tube current-time product, or also some other parameter. A performance parameter may for example relate to a maximum tube power, for example a maximum tube current or a maximum tube current-time product.

Figure 5:
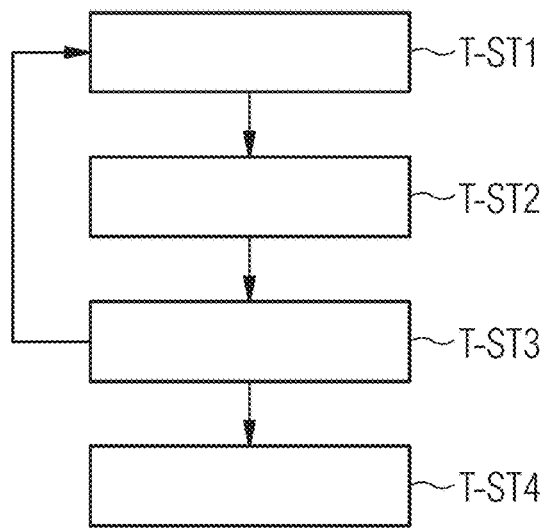
FIG. 5 shows a schematic flow chart for a training method for providing a trained function.

FIG. 5 shows a schematic flow chart for a training method for providing a trained function for application in a method for actuating a medical imaging device for generating an image data set. The training method comprises the first provision step T-ST1, application step T-ST2, adaptation step T-ST3 and second provision step T-ST4.

In the first provision step T-ST1, a training respiratory curve of a training patient and a comparison measurement parameter linked therewith are provided via a training interface T-IF1.

The comparison measurement parameter determines a temporal resolution of a training slice image data set comprised by a training image data set of a training patient for at least one z position comprised by a measurement region when, with application of the comparison measurement parameter, the training image data set is generated via a training imaging device. The measurement region is here affected by respiratory movement. The training slice image data set is here based on a plurality of training projection data sets from various projection angles with relative rotational movement between a radiation source of the training imaging device and the training patient.

In application step T-ST2, the trained function is applied via a training computing unit T-CU to the provided training respiratory curve, wherein a training measurement parameter is derived.

In adaptation step T-ST3, at least one parameter of the trained function is adapted via the training computing unit T-CU based upon a comparison of the derived training measurement parameter and the corresponding comparison measurement parameter.

In the second provision step T-ST4, the trained function is provided via a second training interface T-IF2.

The method may in particular be carried out repeatedly based upon a plurality of training respiratory curves and comparison measurement parameters linked therewith.

Figure 6:
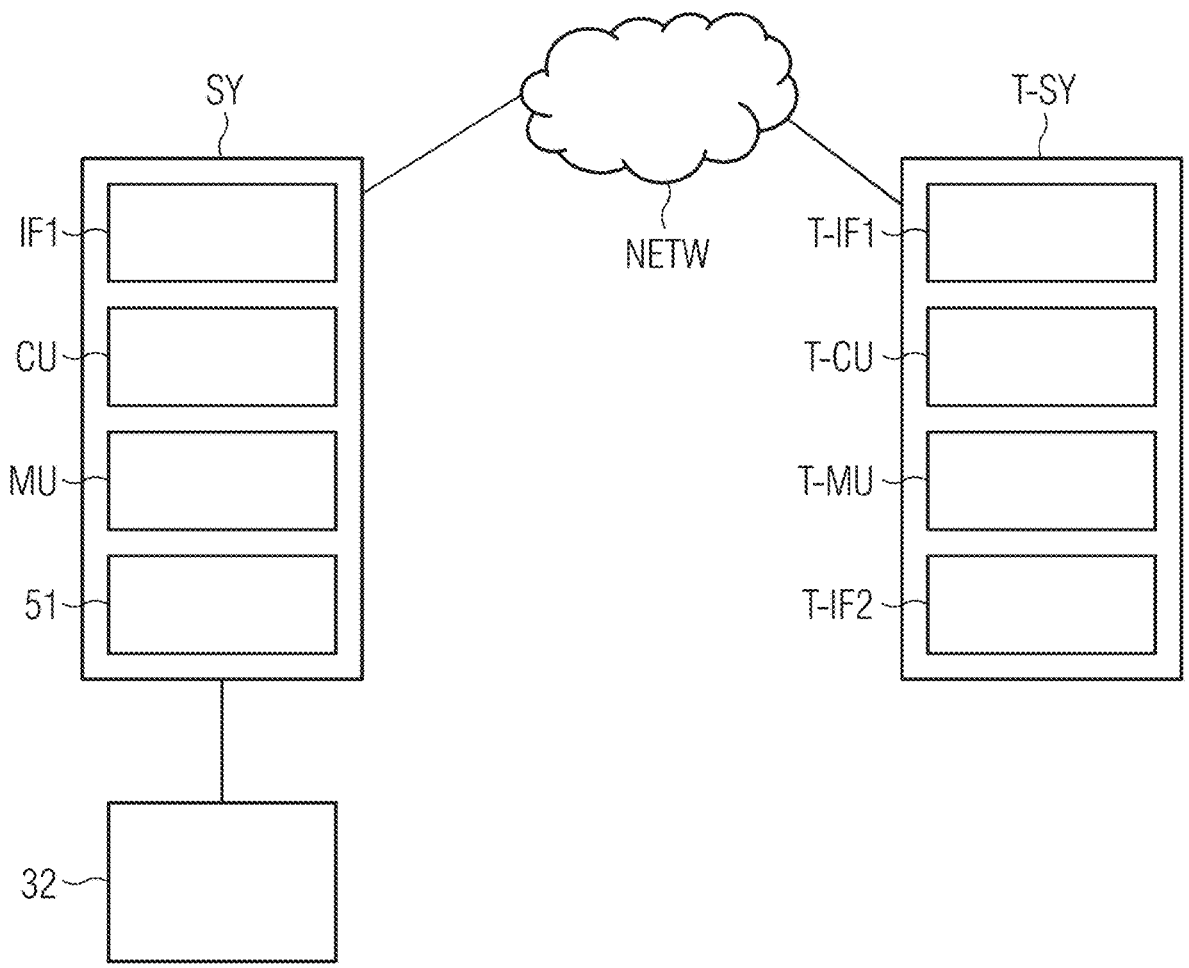
FIG. 6 shows a schematic representation of an apparatus for actuating a medical imaging device and a training apparatus for providing a trained function.

FIG. 6 shows a schematic representation of an apparatus SY for actuating a medical imaging device 32 for generating a patient's 39 measurement region affected by respiratory movement comprising at least one z position, wherein the image data set comprises at least one slice image data set for the at least one z position.

The apparatus SY comprises an interface IF1 configured to provide a respiratory curve S of the patient 39, which describes the patient's 39 respiratory movement over at least one respiratory cycle.

The apparatus SY comprises a computing unit CU configured to automatically derive at least one measurement parameter based upon the provided respiratory curve S, wherein the derived measurement parameter determines a temporal resolution of the at least one slice image data set.

The apparatus comprises a control unit 51 configured to actuate the medical imaging device 32 for generating the image data set based upon the automatically derived measurement parameter, wherein, for the at least one z position, a plurality of projection data sets from various projection angles are acquired with relative rotational movement between a radiation source 37 of the medical device 32 and the patient 39 and, on this basis, the at least one slice image data set of the image data set is generated.

The apparatus SY is to this end coupled for signaling in particular with the medical imaging device 32, such that the medical imaging device 32 is actuatable based upon the at least one measurement parameter or via a control signal based on the at least one measurement parameter.

The apparatus SY is in particular configured for carrying out a proposed method for actuating a medical imaging device 32. The proposed apparatus SY for actuating a medical imaging device 32 may be configured to carry out the variant embodiment of the proposed method for actuating a medical imaging device 32 by the computing unit CU, the interface IF and the control unit 51 being configured to carry out the respective steps of the method.

FIG. 6 moreover shows a training apparatus T-SY for providing a trained function.

The training apparatus T-SY advantageously comprises a first training interface T-IF1, a training computing unit T-CU, a second training interface T-IF2 and a training storage unit T-MU.

The first training interface T-IF is configured to provide T-ST1 a training respiratory curve of a training patient and a comparison measurement parameter linked therewith, wherein the comparison measurement parameter determines a temporal resolution of a training slice image data set comprised by a training image data set of a measurement region affected by respiratory movement of a training patient 39 for at least one z position comprised by the measurement region when, with application of the comparison measurement parameter, the training image data set is generated via a training imaging device, and wherein the training slice image data set is based on a plurality of training projection data sets from various projection angles with relative rotational movement between a radiation source of the training imaging device and the training patient.

The training computing unit T-CU is configured to apply a trained function to the training respiratory curve and so to derive a training measurement parameter. The training computing unit T-CU is furthermore configured to adapt at least one parameter of the trained function based upon a comparison of the derived training measurement parameter and the corresponding comparison measurement parameter.

The second training interface T-IF2 is furthermore configured to provide the trained function.

The represented training unit T-SY is advantageously configured to carry out a proposed method for providing a trained function. The training apparatus T-SY may in particular be configured to carry out the variant embodiment of the method for providing a trained function by the training interfaces T-IF1, T-IF2 and the training computing unit T-CU being configured to carry out the respective steps of the method.

The apparatus SY, a processing unit 45 and/or the training apparatus T-SY may in particular be a computer, a microcontroller or an integrated circuit. It may alternatively here be a computer cluster or cloud. The apparatus SY and/or the training apparatus T-SY may also be configured as a virtual system which is run on a real computer or computer cluster or cloud (virtualization).

The interface IF and/or a training interface T-IF1, T-IF2 may be a hardware or software interface (for example PCI bus, USB or FireWire). A computing unit CU and/or a training computing unit T-CU may have hardware elements or software elements, for example a microprocessor or a field programmable gate array (FPGA). A storage unit MU and/or a training storage unit T-MU may be embodied as volatile working memory or random access memory (RAM) or as non-volatile mass storage (hard disk, USB stick, SD card, solid state disk).

The interface IF and/or a training interface T-IF1, T-IF2 may in particular comprise a plurality of subinterfaces. In other words, the interface IF and/or the training interface T-IF may also comprise a plurality of interfaces IF or a plurality of training interfaces T-IF. The computing unit CU and/or the training computing unit T-CU may in particular comprise a plurality of subcomputing units which carry out the different steps of the respective method. In other words, the computing unit CU and/or the training computing unit T-CU may also be understood as a plurality of computing units CU or a plurality of training computing units T-CU.

In the example embodiment shown, the apparatus SY is connected via a network NETW to the training apparatus T-SY. For example, a function trained via the training apparatus may be transferred via the network NETW to an apparatus. In the example shown, the apparatus SY is furthermore directly coupled with a medical device 32. In particular, the apparatus may also be comprised by the medical device 32. The apparatus SY may, however, also be connected via the network NETW to the medical imaging device 32.

Communication may furthermore also proceed offline between the apparatus SY and the training apparatus T-SY, for example by an exchange of data storage media.

Communication between the apparatus SY and the training apparatus T-SY may for example consist in the apparatus SY transmitting further training data to the training apparatus T-SY or in the training apparatus T-SY transmitting the trained function to the apparatus SY. The training apparatus T-SY may furthermore be connected to other data sources.

The network NETW may be a local area network ("LAN") or a wide area network ("WAN"). One example of a local network is an intranet while one example of a wide area network is the internet. The network NETW may in particular also take wireless form, in particular as a wireless LAN ("WLAN" or "WiFi") or a Bluetooth connection. The network NETW may also take the form of a combination of the stated examples.

An apparatus SY may also comprise a measurement parameter database saved on and retrievable from a storage unit MU which may be accessed via a query. A measurement parameter database may also be stored on an external storage unit. An external storage unit may for example be linked to the apparatus via a network NETW.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for actuating a medical imaging device for generating an image data set of a measurement region of a patient affected by respiratory movement including at least one z position, the image data set including at least one slice image data set for the at least one z position, the method comprising:
provisioning, via a first interface, at least one respiratory curve of the patient, the at least one respiratory curve describing the respiratory movement of the patient over at least one respiratory cycle;
automatically deriving at least one measurement parameter, via a computing device, based upon the at least one respiratory curve, the at least one measurement parameter derived determining a temporal resolution of the at least one slice image data set, the automatically deriving of the at least one measurement parameter includes extracting at least one value comprising a duration of a resting phase of the respiratory movement based upon the at least one respiratory curve, the at least one measurement parameter being derived based upon the at least one value extracted; and
actuating, via a controller, the medical imaging device to generate the image data set based upon the at least one measurement parameter automatically derived, wherein, for the at least one z position, a plurality of projection data sets from various projection angles are acquired with relative rotational movement between a radiation source of the medical imaging device and the patient and, wherein the at least one slice image data set of the image data set is generated based upon the plurality of projection data sets acquired.

2. The method of claim 1, wherein the at least one measurement parameter on which the at least one slice image data set is based includes at least one of
a rotation cycle time of the radiation source during the relative rotational movement and
a projection angle range including an angular range of the various projection angles.

3. The method of claim 1, wherein a dose parameter or a performance parameter of the radiation source enters into the automatically deriving.

4. The method of claim 1, wherein the automatically deriving includes
applying a trained function, at least one parameter of the trained function being adapted to a comparison between a training measurement parameter derived from a training respiratory curve of a training patient and a comparison measurement parameter, the training respiratory curve and the comparison measurement parameter being linked together.

5. The method as claimed in claim 4, wherein the trained function includes a neural network.

6. The method of claim 1, wherein the at least one value extracted includes a duration of an exhalation phase or a gradient of an inhalation phase or exhalation phase.

7. The method of claim 6, wherein the automatically deriving of the at least one measurement parameter based upon the at least one value extracted includes
querying a measurement parameter database stored in a storage unit, wherein the at least one value extracted or a parameter derived from the at least one value extracted is used as a query parameter for the querying.

8. The method of claim 1, wherein the image data set generated includes slice image data sets for a plurality of points in time for the at least one z position and, in the actuating of the medical imaging device to generate the image data set based upon the at least one measurement parameter automatically derived, in each case, a plurality of projection data sets are acquired for each point in time of the plurality of points in time.

9. The method of claim 8, wherein the slice image data sets, of the image data set generated, reproduce the at least one respiratory cycle of the patient over a duration of the at least one respiratory cycle.

10. A training method for providing a trained function, comprising:
provisioning, via a training interface, a training respiratory curve of a training patient and a comparison measurement parameter linked to the training respiratory curve of the training patient, the comparison measurement parameter determining a temporal resolution of a training slice image data set comprised by a training image data set of a measurement region affected by respiratory movement of the training patient for at least one z position comprised by the measurement region, the training slice image data set being generated, via a training imaging device, upon application of the comparison measurement parameter, and the training slice image data set being based on a plurality of training projection data sets from various projection angles with relative rotational movement between a radiation source of the training imaging device and the training patient;
applying, via a training computing device, the trained function to the training respiratory curve to derive a training measurement parameter based on an extracted value comprising a duration of a resting phase of the respiratory movement;
adapting at least one parameter of the trained function, via the training computing device, based upon a comparison of the training measurement parameter derived and a corresponding comparison measurement parameter; and
providing the trained function via a second training interface.

11. A non-transitory computer readable medium comprising instructions, directly loadable into a training storage device of a training apparatus, that when executed by the training apparatus, cause the training apparatus to perform the method of claim 10.

12. An apparatus for actuating a medical imaging device for generating an image data set of a measurement region of a patient affected by respiratory movement including at least one z position, the image data set including at least one slice image data set for the at least one z position, the apparatus comprising:
an interface configured to provide at least one respiratory curve of the patient, the at least one respiratory curve describing respiratory movement of the patient over at least one respiratory cycle;
a computing device configured to automatically derive at least one measurement parameter based upon the at least one respiratory curve, the at least one measurement parameter automatically derived determining a temporal resolution of the at least one slice image data set, the computing device configured to extract at least one value comprising a duration of a resting phase of the respiratory movement based upon the at least one respiratory curve, the at least one measurement parameter being derived based upon the at least one value extracted; and
a controller configured to actuate the medical imaging device to generate the image data set based upon the at least one measurement parameter automatically derived, wherein, for the at least one z position, a plurality of projection data sets from various projection angles are acquired with relative rotational movement between a radiation source of the medical imaging device and the patient and, based upon the plurality of projection data sets acquired, the at least one slice image data set of the image data set is generated.

13. A medical imaging device comprising the apparatus of claim 12.

14. The apparatus of claim 11, wherein a dose parameter or a performance parameter of the radiation source enters into the automatically deriving.

15. The apparatus of claim 12, wherein the computing device is configured to
apply a trained function, at least one parameter of the trained function being adapted to a comparison between a training measurement parameter derived from a training respiratory curve of a training patient and a comparison measurement parameter, the training respiratory curve and the comparison measurement parameter being linked together.

16. The apparatus of claim 15, wherein the trained function includes a neural network.

17. The apparatus of claim 11, wherein the at least one value extracted includes a duration of an exhalation phase or a gradient of an inhalation phase or exhalation phase.

18. The apparatus of claim 17, wherein the computing device is configured to
query a measurement parameter database stored in a storage unit, wherein the at least one value extracted or a parameter derived from the at least one value extracted is used as a query parameter for the querying.

19. A training apparatus for providing a trained function for application, comprising:
a first training interface configured to provide a training respiratory curve of a training patient and a comparison measurement parameter linked with the training respiratory curve of the training patient, the comparison measurement parameter determining a temporal resolution of a training slice image data set comprised by a training image data set of a measurement region affected by respiratory movement of the training patient for at least one z position comprised by the measurement region, the training image data set being generated via a training imaging device upon application of the comparison measurement parameter and the training slice image data set being based on a plurality of training projection data sets from various projection angles with relative rotational movement between a radiation source of the training imaging device and the training patient;
a training computing device configured to apply the trained function to the training respiratory curve to derive a training measurement parameter based on an extracted value comprising a duration of a resting phase of the respiratory movement, and further configured to adapt at least one parameter of the trained function based upon a comparison of the training measurement parameter derived and a corresponding comparison measurement parameter; and
a second training interface configured to provide the trained function.

20. A non-transitory computer readable medium comprising instructions, directly loadable into a storage device of an apparatus for actuating a medical imaging device, that when executed by the apparatus, cause the apparatus to perform the method of claim 1.

* * * * *